United States Patent [19]

Schmolka

[11] 4,395,393

[45] Jul. 26, 1983

[54] ARTIFICIAL BLOOD EMULSIFIERS

[75] Inventor: Irving R. Schmolka, Grosse Ile, Mich.

[73] Assignee: BASF Wyandotte Corporation, Wyandotte, Mich.

[21] Appl. No.: 291,264

[22] Filed: Aug. 10, 1981

[51] Int. Cl.³ .................... A61K 31/74; A61K 31/02
[52] U.S. Cl. ..................................... 424/78; 424/325; 424/350
[58] Field of Search .......................... 424/78, 350, 325

[56] References Cited

U.S. PATENT DOCUMENTS 4,110,474  8/1978  Lagow et al. ....................... 424/350

Primary Examiner—Sam Rosen
Attorney, Agent, or Firm—Bernhard R. Swick

[57] ABSTRACT

An artificial blood composition comprises a perfluoro chemical, physiological saline and a polyoxybutylene-polyoxyethylene block copolymer. The block copolymer provides stable emulsions.

6 Claims, No Drawings

ARTIFICIAL BLOOD EMULSIFIERS

BACKGROUND OF THE INVENTION

1. Field of the Invention

Artificial blood compositions are prepared from certain perfluoro chemicals in physiological saline using certain polyoxybutylene-polyoxyethylene block copolymers. These clock copolymers provide stable emulsions.

2. Description of the Prior Art

In an article by Irving R. Schmolka entitled, "Introduction to Artificial Blood Materials", from session 1 of a symposium on artificial blood presented at the Blood Resource Branch for National Heart and Lung Institute, NIH, Bethesda, Maryland, April 5–6, 1974, polyoxypropylene-polyoxyethylene block polymers are disclosed as being useful emulsifiers for perfluoro chemicals in synthetic blood preparations.

The HS symposium, "Research in Perfluoro Chemicals in Medicine Biology", Apr. 28–29, 1977 at Karolinska Institute Research Center, Huddinge University Hospital in Huddinge, Sweden, was directed to fluoro chemicals, in particular perfluorodecalin. A paper related to emulsions with polyoxypropylene-polyoxyethylene block copolymer emulsifiers. Although it is possible to emulsify perfluorodecalin in physiological saline, using a block polymer of ethylene and propylene oxides, the resulting emulsion is not stable. The reference relates to the use of a blend of perfluorodecalin and perfluorotripropylamine (FTPA) in artificial blood preparations to overcome the emulsion instability. Unfortunately, the FTPA has a low vapor pressure and accumulates in the liver which is not desirable.

U.S. Pat. No. 4,110,474 relates to perfluorinated 2,2,4,4-tetramethylpentane useful in synthetic blood substitute compositions. The use of polyoxybutylene-polyoxyethylene block copolymers as emulsifiers is not mentioned.

U.S. Pat. No. 4,105,798, Moore et al, Aug. 8, 1978, relates to perfluorinated compounds useful in synthetic blood in perfusion media. Polyoxybutylene-polyoxyethylene block copolymers are not mentioned as emulsifiers.

Both patent reference U.S. Pat. Nos. 4,105,798 and 4,110,474 utilize a polyoxypropylene-polyoxyethylene block copolymer known as PLURONIC F68. Some of the problems utilizing this copolymer are enumerated above. This invention is directed towards stable emulsions of perfluoro chemicals devoid of the prior art problems.

SUMMARY OF THE INVENTION

The invention relates to an artificial blood composition comprising a polyoxybutylene-polyoxyethylene block copolymer emulsifier, a perfluoro chemical suitable for artificial blood preparation and physiological saline, said emulsifier being a cogeneric mixture of conjugated polyoxybutylene-polyoxyethylene compounds containing in their structure oxybutylene groups, oxyethylene groups and an organic radical derived from an organic compound containing a plurality of reactive hydrogen atoms, preferably a water soluble organic compound containing a plurality of reactive hydrogen atoms and 2 to 12 carbon atoms. The compounds are characterized in that all the oxybutylene groups are present in polyoxybutylene chains that are attached to the organic radical at the site of a reactive hydrogen atom thereby principally constituting a polyoxybutylene polymer. The oxyethylene groups are attached to the polyoxybutylene polymer in polyoxyethylene chains. The average molecular weight of the polyoxybutylene polymers in the mixture is from about 600 to about 3000, as determined by hydroxyl number, and the oxyethylene groups present constitute between about 60 percent and about 85 percent by weight of the compound. These artificial blood products surprisingly provide a stable emulsion of perfluoro chemical alone with the aqueous solution of a polyoxybutylene-polyoxyethylene block copolymer.

DESCRIPTION OF THE PREFERRED EMBODIMENTS

The block copolymer of use in the invention is a cogeneric mixture of conjugated polyoxybutylene-polyoxyethylene compounds having as a hydrophobe, a polyoxybutylene polymer of at least 500 molecular weight. The polyoxybutylene compounds are prepared by first condensing butylene oxide with an organic compound containing a plurality of reactive hydrogen atoms to prepare a polyoxybutylene polymer of at least 500 molecular weight, and subsequently condensing ethylene oxide thereto. The compounds used in this invention conform to the following generic formula:

$$Y[(C_4H_8O)_n\text{-}E\text{-}H]_x \qquad (A)$$

wherein Y is the residue of a water-soluble organic compound containing therein x active hydrogen atoms; n is an integer; x is an integer greater than 1; the values of n and x are such that the molecular weight of the compound, exclusive of E, is at least 500, as determined by hydroxyl number; E is a polyoxyalkylene chain wherein the oxygen/carbon atom ratio is at least 0.5, and E constitutes 60 percent by weight to 85 percent by weight of the compound.

The polyoxybutylene polymer, which is an intermediate in the preparation of the compounds of use in this invention, has the following structure:

$$Y[(C_4H_8O)_nH]_x \qquad (B)$$

wherein Y, n and x are defined as in Formula A above.

The preferred compounds of use in this invention are prepared by condensing ethylene oxide in an amount between 60 and 85 percent by weight of the resultant compound, with the polyoxybutylene polymer. These compounds have the following formula:

$$Y[(C_4H_8O)_n(C_2H_4O)_mH]_x \qquad (C)$$

wherein Y, n and x are defined as in Formula A and m has a value such that the oxyethylene groups constitute 60 to 85 percent by weight of the compound.

When ethylene oxide is condensed with a polyoxybutylene glycol of at least 500 molecular weight and derived from a butanediol initiator, the resulting compounds have the following structure:

$$HO(C_2H_4O)_{m'}(C_4H_8O)_n(C_2H_4O)_mH \qquad (D)$$

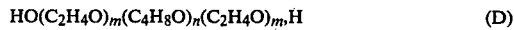

where n is defined as previously set forth; and $m'+m$ have a value such that the oxyethylene groups constitute 60 percent by weight to 85 percent by weight of the compound.

The hydrophilic portion of the polyoxyalkylene compounds may be supplied in whole or in part by other polyoxyalkylene chains in lieu of the polyoxyethylene chain set forth in Formula C. Any polyoxyalkylene chain may be used provided that the oxygen/carbon ratio contained therein is at least 0.5.

Examples of a water-soluble organic compound containing therein x active hydrogen atoms, the residue of which is Y, are the initiators, which may include water, diols such as propane diol, butane diol, triols such as glycerol, tetrols such as pentaerythritol as well as initiators containing more than four hydroxyl groups such as hexitol or sucrose. Also, amines and other low molecular weight water-soluble compounds having two or more active hydrogen atoms such as ethylene diamine or diethylene triamine may be used as the initiator. Preferably used is butane diol. More perferably used is 1,4-butanediol.

The butylene oxide used in making the hydrophilic polyoxybutylene polymer, which is an intermediate in the preparation of the compounds used in this invention, may be replaced with up to 10 percent by weight of propylene oxide or ethylene oxide when added as a mixture with the butylene oxide. Also, up to 10 percent by weight of propylene oxide or butylene oxide may be used to replace ethylene oxide, when added as a mixture with ethylene oxide, in preparing the block copolymers used in this invention. In lieu of butylene oxide, other 4-carbon cyclic ethers such as methyloxetane, tetrahydrofuran and isobutylene oxide may be used.

The preferred block copolymers conforming to structure D above of use in this invention, are those block copolymers which contain a hydrophobe of between about 500 and 3000, preferably 1200 and 1800, average molecular weight and between about 60 percent by weight and about 85 percent by weight, preferably about 80 percent by weight, ethylene oxide. The emulsifier is used in an amount between 0.05 percent by weight to 10 percent by weight, preferably 2 percent by weight to 8 percent by weight, more preferably 4 percent by weight to 6 percent by weight of the artificial blood composition.

The perfluoro chemical found most suitable for artificial blood preparations is perfluorodecalin (FDC). This material leaves the body rapidly due to its high vapor pressure. It is excreted through the breath and the skin. Emulsions of FDC, heretofore not stable with prior art emulsifiers, have now been found unexpectedly to be stable when the emulsifier is the polyoxybutylene-polyoxyethylene block copolymer of the invention. Other perfluoro chemicals which may be used include perfluoromethyldecalin, perfluorotributylamine and perfluoro 2,2,4,4-tetramethyl pentane. The perfuoro chemical is used in an amount between 10 percent by weight and 40 percent by weight of the artificial blood composition.

The saline solution of use in the artificial blood of this invention may be any suitable physiological saline solution. The components may include sodium chloride, magnesium chloride, potassium chloride, sodium lactate, glucose and water. The saline solution is used as an electrolyte solution in the artificial blood in an amount between 40 to 80 percent by weight of the artificial blood composition.

Additional emulsifying agents may be used in a combination of emulsifiers with polyoxybutylene-polyoxyethylene block copolymers of this invention. Suitable additional emulsifying agents are the polyoxypropylene-polyoxyethylene block copolymer designated as PLURONIC Polyols and egg-yolk phospholipid.

The artificial blood compositions of this invention are prepared from 2 to 8 percent by weight of block copolymer emulsifier, 10 to 40 percent by weight of perfluoro chemical and from 40 to 80 percent by weight of physiological saline solution, preferably a 2 to 8 percent physiological saline solution. An emulsion may be made as follows: the block copolymer emulsifier is dissolved in water and then the perfluoro chemical is added. The mixture is stirred by a suitable means such as sonication, under a carbon dioxide atmosphere, for a suitable period of time, such as two hours, to produce an optically clear stable emulsion of fine particles of perfluoro chemical. The emulsions have a fine particle size of 0.3 microns or less in diameter. The electrolyte solution is blended in any suitable blender with perfluoro chemical in an amount of about 10 volume percent of electrolyte solution and about 90 volume percent of emulsion.

The following examples will further illustrate the various aspects of the invention. Where not otherwise specified throughout the specification and claims, temperatures are in degrees Centigrade and parts, percentages and proportions are by weight.

The following block copolymers are used in the examples:

| Block Copolymer | Average MW of Polyoxybutylene Hydrophobe | Percent by weight of Ethylene Oxide |
|---|---|---|
| A | 600 | 80 |
| B | 1200 | 70 |
| C | 1200 | 80 |

EXAMPLE 1

Peparation of an Artificial Blood Composition

The following aqueous solution is prepared:

| | |
|---|---|
| NaCl | 6.0 grams |
| $MgCl_2$ | 0.2 gram |
| KCl | 0.3 gram |
| Sodium lactate | 3.1 grams |
| Glucose | 1.0 gram |
| Water | to 100 ml |

The following perfluorocarbon emulsion is prepared:

| | |
|---|---|
| Perfluorodecalin | 18 grams |
| Block copolymer A | 5 grams |
| Water | to 100 ml. |

The emulsion is made by dissolving the block copolymer A in the water, and then adding the perfluorodecalin. The mixture is sonicated under a carbon dioxide atmosphere for two hours to produce an optically clear stable emulsion of fine particles of perfluorodecalin. For use as an artificial blood, 10 ml of the electrolyte solution is blended with 90 ml of the fluorocarbon emulsion.

EXAMPLES 2-6

An artificial blood composition is prepared by a procedure similar to Example 1 from the following components:

| Percent by Weight | Component |
| --- | --- |
| 5 | Block Copolymer A |
| 19 | Perfluorodecalin |
| 76 | 5% Saline Solution |
| 6 | Block Copolymer B |
| 18 | Perfluoromethyldecalin |
| 76 | 3% Saline Solution |
| 4 | Block Copolymer C |
| 20 | Perfluoro 2,2,4,4-tetramethylpentane |
| 76 | 4% Saline Solution |

| Amount | Component |
| --- | --- |
| 30 grams | Perfluoromethyldecalin |
| 7 grams | Block copolymer C |
| to 100 ml | Water |

An artificial blood composition is prepared complete with no dilution.

| Amount | Component |
| --- | --- |
| 12 ml | Perfluorotributylamine |
| 2.5 grams | Block copolymer A |
| 3.0 grams | Hydroxyethyl starch |
| 54 mg | NaCl |
| 32 mg | KCl |
| 7 mg | MgCl$_2$ |
| 10 mg | CaCl$_2$ |
| 9.6 mg | NaH$_2$PO$_4$ |
| to pH 7.45 | Na$_2$CO$_3$ |
| to 100 ml | Water |

Stable emulsion are obtained which maintain their stability over long periods of time.

The embodiments of the invention in which an exclusive privilege or property is claimed are defined as follows:

1. An artificial blood comprising from 10 to 40 percent by weight of a perfluoro chemical, from 40 to 80 percent by weight physiological saline and from 2 to 8 percent by weight of a polyoxybutylene-polyoxyethylene block copolymer emulsifier, said emulsifier being a cogeneric mixture of conjugated polyoxybutylene-polyoxyethylene compounds containing in their structure oxybutylene groups, oxyethylene groups and an organic radical derived from a water-soluble organic compound containing a plurality of reactive hydrogen atoms and 2 to 12 carbon atoms; the compounds being characterized in that all of the oxybutylene groups are present in polyoxybutylene chains that are attached to the organic radical at the site of a reactive hydrogen atom thereby constituting a polyoxybutylene polymer; the oxyethylene groups being attached to the polyoxybutylene polymer in polyoxyethylene chains; the average molecular weight of the polyoxybutylene polymers in the mixture being between about 1200 and 3000, as determined by hydroxyl number, and the oxyethylene groups present constituting 60 to 85 percent by weight of the mixture.

2. The artificial blood of claim 1 wherein the perfluoro chemical is selected from the group consisting of perfluorodecalin, perfluoromethyldecalin, perfluorotributylamine, and perfluoro 2,2,4,4 tetramethyl pentane.

3. The artificial blood of claim 2 wherein the polyoxybutylene polymer has a molecular weight of about 1200.

4. The artificial blood of claim 2 wherein the polyoxybutylene polymer has a molecular weight of about 1800.

5. The artificial blood of claim 1 wherein the perfluoro chemical is perfluorodecalin and the polyoxybutylene polymer has a molcular weight of about 1200 and the oxyethylene content is about 80 percent by weight of the mixture.

6. The artificial blood of claim 1 wherein the perfluoro chemical is perfluorodecalin and the emulsifier polyoxybutylene polymer has a molecular weight of about 1800 and the oxyethylene content is about 80 percent by weight of the mixture.

* * * * *